United States Patent [19]

Goodman et al.

[11] 4,116,949
[45] Sep. 26, 1978

[54] WATER-SOLUBLE, PHYSIOLOGICALLY ACTIVE, SYNTHETIC COPOLYPEPTIDES

[75] Inventors: Murray Goodman, La Jolla; Michael S. Verlander, Del Mar; Nathan O. Kaplan, La Jolla; J. Craig Venter, Solana Beach, all of Calif.

[73] Assignee: The Regents of the University of California, Berkley, Calif.

[21] Appl. No.: 679,032

[22] Filed: Apr. 21, 1976

[51] Int. Cl.$^2$ .................. C07C 103/52; A61K 37/00
[52] U.S. Cl. .......................... 260/112.5 R; 424/177
[58] Field of Search ................ 260/112.5 R; 424/177

[56] References Cited

U.S. PATENT DOCUMENTS 3,304,296  2/1967  Schuyzer et al. ............. 260/112.5 R

OTHER PUBLICATIONS

Wagner, et al.; Syn. Org. Chem., p. 764.
Wagner, et al.; Syn. Org. Chem., pp. 654–655.
Wagner, et al.; Syn. Org. Chem., pp. 772–773.

Primary Examiner—Delbert R. Phillips

Attorney, Agent, or Firm—Larson, Taylor and Hinds

[57] ABSTRACT

Water-soluble copolypeptides having high physiological activity for prolonged periods of time comprise water-soluble, linear copolypeptides having attached to their polymeric backbone at least one substituent having the structure:

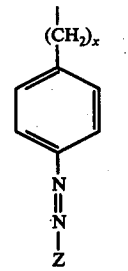

wherein Z is an aromatic group derived from a physiologically active compound and x is an integer and equal to 0 or 1.

12 Claims, 1 Drawing Figure

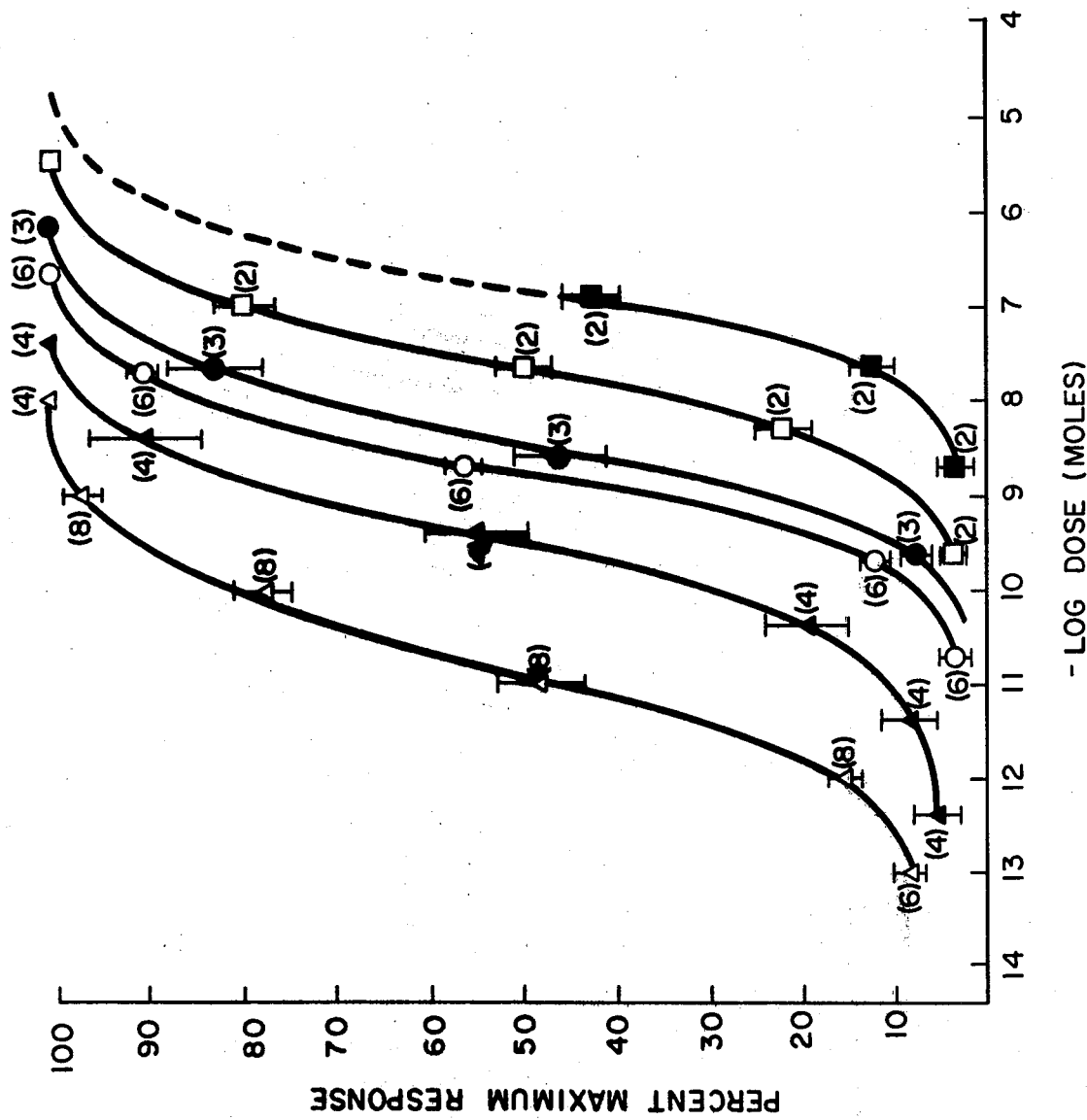

WATER-SOLUBLE, PHYSIOLOGICALLY ACTIVE, SYNTHETIC COPOLYPEPTIDES

FIELD OF THE INVENTION

The invention relates to water-soluble, physiologically active, synthetic polypeptides and to a method for their preparation. More particularly the present invention is directed to water-soluble, synthetic polypeptides having covalently bonded thereto via azo linkages a physiologically active compound such as a catecholamine.

BACKGROUND OF THE INVENTION

The literature is replete with proposals from researchers attempting to extend the active life of compounds possessing physiological activities by coupling the compounds to large natural and synthetic materials. None of these attempts, however, have met with singular success.

U.S. Pat. No. 3,704,282 to Sidney Spector, for instance, describes the failure of others in preparing an antigen by diazotizing aminoadrenaline and coupling the resulting diazoadrenaline with a serum albumin. The resulting product was reported as being inactive because of the absence of the essential catechol function of aminoadrenaline and as not being an antigen specific for adrenaline, containing most likely an oxidized catechol function such as an orthoquinone. Spector emphasizes that this product is of limited utility as an effective antigen and chooses instead to bond the biologically active compound, i.e., the catecholamine to the polymer through a peptide linkage.

Water-soluble polymer-hormone products containing a hormone covalently bonded to a copolymer of an olefinically unsaturated polycarboxylic acid and an olefin also are reported in Schuck et al., U.S. Pat. No. 3,679,653. In the teachings of Schuck et al., the hormone is covalently bonded to the polymer through either amino, hydroxyl, or sulfhydryl groups of the hormone. Specifically, the preferred polymers are either ethylene/maleic anhydride copolymers or styrene/maleic anhydride copolymers with the preferred hormone being either peptidic or proteinaceous.

Another method for covalently bonding a hormone to the polymer has been set forth by Lennart Kagedal in U.S. Pat. No. 3,788,948. In accordance with the teachings of Kagedal, the biologically active hormone is covalently bonded to a polysaccharide by a urethane group. E. Katchalski, in his article "Preparation, Properties and Applications of Some Water-Insoluble Derivatives of Proteolytic Enzymes" in *Polyaminoacids, Polypeptides and Proteins*, 1962, pp. 283-289, describes proteolytic enzymes bonded via azo linkages to copolypeptides. The products of Katchalski, however, are water-insoluble immobilized enzymes designed as biological catalysts which obviates their use as physiologically active compounds.

Thus, each of the aforementioned methods fails to provide a product which possesses the desired physiological activity while simultaneously providing long-lasting effects.

OBJECTS

It is an object of this invention to provide a water-soluble synthetic copolypeptide having covalently bonded thereto a physiologically active component which copolypeptide displays increased duration of activity when compared to the physiologically active components in its free or uncombined form.

Another object of the invention is to provide a water-soluble copolypeptide derivative of a physiologically active component which provides physiological activity per unit of the active component bound to the copolypeptide which is comparable to or greater than that of the free or unbound physiologically active component.

A further object of the invention is to provide a product which not only possesses the aforementioned high degree of physiological activity but makes the active component available in a controlled manner over a prolonged period of time so as to give long-lasting physiological activity.

Yet another object of the invention is to provide a method whereby water-soluble, physiologically active copolypeptides can be tailor-made with a high degree of reproducibility to suit a given application. It is possible to prepare water-soluble, physiologically active copolypeptides which exhibit altered sites and duration of physiological activity because of the predetermined compositions of the copolypeptides.

SUMMARY OF THE INVENTION

These and other objects of the invention are achieved by a water-soluble, physiologically active polymer comprised of a linear, water-soluble copolypeptide having attached to the copolypeptide backbone at least one substituent having the structure:

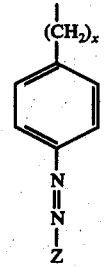

wherein Z is an aromatic group derived from a physiologically active compound and $x$ is an integer and equal to 0 or 1. By physiologically active, we mean exertion of an effect in a physiological system.

The novel polymeric products of the invention can be prepared, for instance, by subjecting a water-soluble, linear copolypeptide containing at least one and preferably a plurality of aromatic amine substituents attached to its backbone to diazotization to form a diazonium salt thereof which is then allowed to react with the physiologically active compound having an aromatic nucleus with a $\pi$-electron density greater than benzene. An example of the synthesis can be represented as follows:

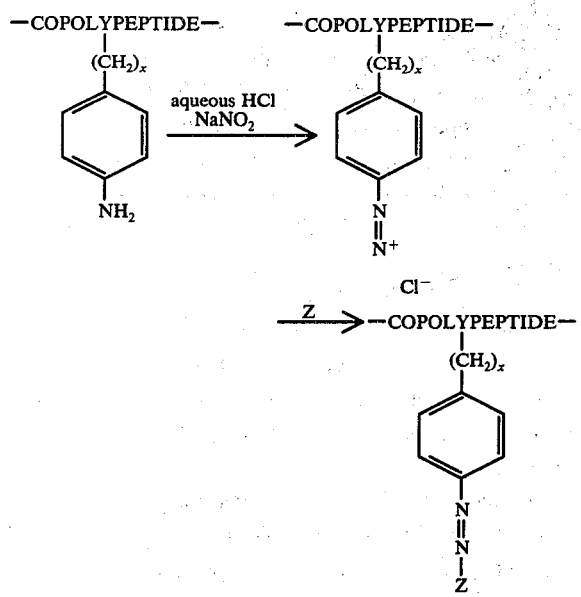

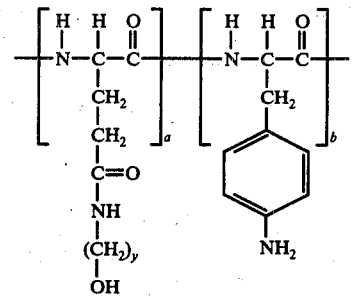

The copolypeptides to which the physiologically active group is covalently bonded are water-soluble, preferably non-ionic, synthetic copolypeptides comprising an aromatic amine-substituted amino acid and at least one dissimilar amino acid. While they may be formed by allowing the aromatic amine-substituted amino acid to react with one or a mixture of dissimilar amino acids, it is preferred to prepare the copolypeptides by first allowing an amino acid derivative to react with an amino acid containing an aromatic substituent convertible to an aromatic amine as, for instance, a nitroaromatic group. The resulting nitroaromatic group-containing copolypeptides, according to one aspect of the method of the invention, are subjected to a reduction whereby the nitroaromatic groups are converted to aromatic amine groups. Thus, the only essential requirements imposed on the selection of the amino acid monomers are that at least one of them contain an aromatic amine (or aromatic substituent convertible to an aromatic amine) and the amino acid type and/or ratio of amino acids employed be such as to render the resulting copolypeptides water-soluble. Water-solubility in the copolypeptides may be conferred by selecting amino acids and mixtures thereof containing groups such as hydroxylalkylglutamine groups, carboxyl groups, alkylene oxide groups, and the like or having groups which can subsequently be converted into such groups. Alternatively, the necessary water-solubility-inducing groups may be added to the copolypeptides through suitable reaction with reactive sites on the copolymer.

Illustrative of suitable aromatic amino- or nitroaromatic group-containing amino acids which can be employed in the present invention are p-aminophenylalanine, p-aminophenylglycine, p-aminophenylglutamine, p-aminobenzoyllysine, p-nitrophenylalanine, p-nitrophenylglycine, p-nitrobenzoyllysine and the like.

Exemplary of amino acids, one or more of which can be allowed to react with the aromatic amine or nitroaromatic group-containing amino acid monomer are glutamic acid, benzylglutamic acid, alanine, glutamine, leucine, phenylalanine, lysine, tyrosine, valine, asparagine, glycine, etc.

Illustrative of the preferred copolypeptides in accordance with the present invention are copolypeptides comprising irregular copolymers of hydroxyalkylglutamines with p-aminophenylalanine as illustrated by the structure:

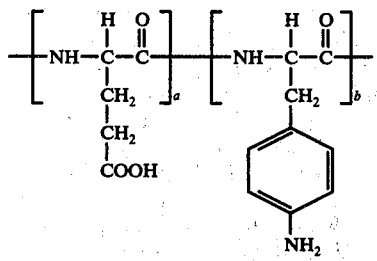

wherein $y$ is an integer of 2 or 3 and $a$ and $b$ are integers, the ratio of $a$ to $b$ being in the range 1:1 to 25:1.

Another preferred class of copolypeptides in accordance with the present invention are copolypeptides comprising irregular copolymers of glutamic acid with p-aminophenylalanine as illustrated by the structure:

wherein $a$ and $b$ are integers, the ratio of $a$ to $b$ being in the range 1:1 to 25:1. The preferred range of the ratio of $a$ to $b$ in both cases is 4:1 to 10:1.

The polymerization of the amino acid monomers may be effected by any of the conventional methods of polypeptide synthesis. One method, for example, which was introduced by Bergmann and Zervas in 1932, comprises acylation by benzyl chlorocarbonate, heating with phosphorus pentachloride, and polymerization of this activated monomer. The conditions necessary for effecting polymerization of the amino acids will be dependent on the method selected and have been extensively reported in the literature. An important consideration in the method of the present invention, however, in selecting a method for polypeptide synthesis is that the aromatic amine group of the amino acid be protected so as to prevent side reactions. Alternatively, preferred procedures utilize the aromatic nitro-containing amino acids for polymerization which can be subsequently converted to aromatic amine groups in the resultant polymers.

Advantageously, the copolypeptides employed in the present invention are prepared from the corresponding N-carboxyanhydride derivatives of the respective amino acid monomers, hereinafter referred to as NCAs, which can be prepared conveniently by treating the amino acids with phosgene. The NCA of the preferred protected amino-aromatic or nitro-aromatic amino acid can be represented as follows:

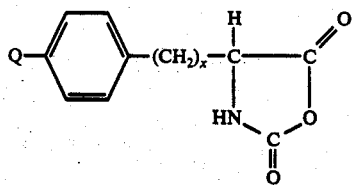

wherein Q is —NO₂ or —NHB, wherein B is a suitable protecting or blocking group, and x is an integer and equal to 0 to 1. Illustrative of standard blocking groups B are carbobenzoxy, t-butyloxycarbonyl, acetyl and the like.

Illustrative of the preferred amino acid NCAs with which the above aromatic amine- or aromatic nitro-containing NCA may be copolymerized are NCAs which may be represented as follows:

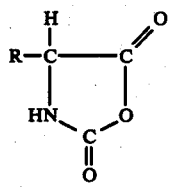

wherein R can be lower alkyl of 1 to 5 carbon atoms or aryl, preferably substituted or unsubstituted benzyl. The preferred R substituents include

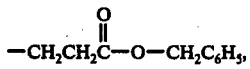

—CH₂CH₂CH₂CH₂NH—B, wherein B is defined as above, —CH₂OCH₂C₆H₅, and the like. In addition, the amino acids used may be either of the naturally-occurring L- or the D-configuration or a mixture of both.

The polymerization or condensation reaction of the NCA can be conducted simply by adding the reactants to a suitable inert liquid diluent with or without a catalyst, preferably under anhydrous conditions. Preferably the inert liquid diluent is an organic solvent for the starting materials but may be a non-solvent for the polymeric products. Suitable inert liquid diluents which can be used include, for example, aromatic hydrocarbons such as benzene, toluene and the like; chlorinated hydrocarbons such as chlorobenzene; ethers, such as dioxane; and organic solvents such as dimethyl formamide, dimethyl sulfoxide and the like. Other suitable diluents will be obvious to those skilled in the art.

Although the polymerization may be conducted in the absence of a catalyst or initiator, use of a catalyst is preferred and in most instances necessary. Suitable catalysts include dibenzyl glutamate, n-butylamine; tertiary amines such as triethylamine, tributylamine, triamylamine, pyridine, N,N-dimethyl aniline, etc; alkali metal alkoxides such as sodium methoxide or sodium ethoxide; and strong bases such as sodium hydroxide or potassium hydroxide and the like. The concentration of the catalyst may vary widely. Generally the concentration of catalyst falls in the range of about 0.01% to 20% by weight.

If a nitroaromatic group containing amino acid or derivative thereof is employed in the polymerization, the resulting copolypeptide is reduced using conventionl reducing techniques such as by subjecting the copolypeptide to hydrogenation in the presence of a hydrogenation catalyst and under hydrogenation conditions.

Following the formation of aromatic amine group-containing copolypeptides, at least one of the aromatic amines is diazotized. The diazotization can be effected by any of the well known processes reported on in the literature. A satisfactory method involves the treatment by nitrous acid followed by the addition of a mildly alkaline buffer solution, pH approximately 7.5. The diazotized polypeptide can then be successfully linked through the azo compound to a physiologically active, π-electron rich aromatic nucleus.

The physiologically active, π-electron rich aromatic nucleii that are suitable for the present invention are characterized in that they are susceptible to electrophilic attack by the aromatic diazonium ion. Active members of this class include, for instance, phenols, catechols, aromatic amines, alkyl- and aryl-ethers derived from phenols and alkyl-substituted aromatics.

Examples of physiologically active aromatic compounds which fall into this classification include but should not be limited to the following:
catecholamines such as epinephrine, norepinephrine, and isoproterenol analgesics such as morphine and related alkaloids
antibiotics such as ampicillin, tetracyclines and sulfanilamides steroids such as estrogen, estriol, etc.
anti-hypertensive agents such as reserpine or α-methyl dihydroxyphenylalanine
anti-Parkinsonism agents such as L-dihydroxyphenylalanine and its derivatives
serotonin and related compounds
hypoglycemic agents such as carbutamide
tyrosine-containing peptide hormones such as angiotensin, insulin, gastrin, etc.
hallucinogens such as substituted phenethylamines The value of the present invention can be demonstrated by reference to the catecholamines which are well known hormones that have enjoyed widespread use as heart stimulants. However, these hormones must be continuously injected into the system when utilized because of their limited active life. It has now been discovered that when a catecholamine, such as epinephrine, norepinephrine, isoproterenol, etc., is linked through an azo linkage to at least one of the aromatic substituents of a water-soluble copolypeptide pursuant to the present invention, the duration of action to the catecholamine is significantly increased often up to 10 times that of the parent catecholamine.

The polymer backbone is responsible for the noted increase in duration of activity. It is believed that this increase in duration of activity may be caused by protection by the polypeptide of the physiologically active compound from degradation. Fruther, the physiological response is modified because it is believed that the polymer affects the diffusion of the hormone into the tissue.

The composition of the polypeptide, especially its molecular weight, is determinative of the specific activity of the derivative, i.e. physiological activity per unit of physiologically active nucleus bound to the polymer. Some of the other factors which affect the specific activity of the compounds are the chemical nature of the amino acid components of the copolypeptide, the functional groups composing the polymer and the charge on those functional groups. While the molecular weight of the copolypeptides can vary widely from 1,000 to 100,000 or more, it has been found that the most active preparations are those having a molecular weight of less than about 20,000, preferably about 1,500 to 10,000.

The copolypeptides of the invention are found to possess physiological activity whenever a single physiologically active aromatic group —Z is present. It is preferred, however, that the number of the azo aromatic groups,

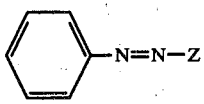

present in the copolypeptide by sufficient to provide in the polymer about 0.5 to 20% by weight of the active component.

The following examples are included to further illustrate the present invention.

EXAMPLE I

γ-Benzyl-L-glutamic acid N-carboxyanhydride and L-p-nitrophenylalanine anhydride were prepared by standard phosgenation procedures. The anhydrides were copolymerized as a 10% (w/v) solution in dry dioxane by mixing 80% (molar) γ-benzyl-L-glutamic acid N-carboxyanhydride with 20% (molar) L-p-nitrophenylalanine N-carboxyanhydride. Dibenzyl glutamate was used to initiate the polymerization (monomer : initiator ratio = 5–50). Following the completion of the polymerization, the reaction mixture was diluted with 2 volumes of anhydrous propanolamine and stirred at room temperature for 24 hours in order to remove the benzyl ester protecting group and render the polymer water-soluble. A water-soluble copolypeptide containing hydroxypropylglutamine and p-nitrophenylalanine was precipitated by pouring the reaction mixture into 20 volumes of dichloroethane and dried in vacuo.

EXAMPLE II

The procedure of Example I was followed using sodium methoxide as initiator (monomer : initiator ratio = 50–200) and using 95% ethanol to precipitate the polymer. The benzyl ester protecting group was removed by dissolving the polymer in anhydrous benzene, treating with dry hydrogen bromide gas and evaporation of the solvents. A water-soluble copolypeptide containing glutamic acid and p-nitrophenylalanine was obtained by dissolving the polymer in 0.1 M sodium hydroxide and dialysis against water and lyophilization.

EXAMPLE III

The polymer of either Examples I or II was reduced by dissolving the polymer in water, acidifying the solution to a pH of approximately 4.5 and hydrogenating the polymer under a pressure of 50 psi for 20 hours in the presence of a 10% palladium on charcoal catalyst (approximately 10% of the weight of the polymer). The solution was filtered through celite and evaporated to dryness in vacuo. A copolypeptide containing either glutamic acid or hydroxypropylglutamine and p-aminophenylalanine was obtained.

EXAMPLE IV

The polymer of either Examples I and II were reduced by treating a solution of 2 g of the polymer in 0.5 M NaHCO$_3$ (50 ml) with 5% (w/v) sodium dithionite at 50° C for 1 hour. A copolypeptide, as in Example III, containing either glutamic acid or hydroxypropylglutamine and p-aminophenylalanine was obtained, following purification of the low molecular weight material by gel chromatography or dialysis.

EXAMPLE V

Copoly(hydroxypropylglutamine: p-aminophenylalanine) (100 mg) formed by the method of either Examples III or IV was dissolved in 2 ml of 0.25 M hydrochloric acid, cooled in an ice-salt bath and diazotized with 0.5 ml of .5 M sodium nitrite. After 15 minutes the solution was buffered to a pH of 7.5 by the addition of 1 ml of 0.5 M phosphate buffer, pH 7.5 and 0.4 ml of 1 M sodium hydroxide. A solution of 50 mg of isoproterenol in 1 ml of 0.25 M phosphate buffer (pH 7) was then added. The solution was stirred overnight at 4° C with the exclusion of light. The product containing a physiologically active linear polypeptide having isoproterenol attached to its backbone was purified by gel chromatography. The product contained 1–10% by weight of isoproterenol.

EXAMPLE VI

The polypeptide derivative prepared in Example V which contains copolymers of hydroxypropylglutamine and p-aminophenylalanine to which isoproterenol was bound through an azo linkage was injected into a perfused guinea pig heart. The stimulation of the heart was compared with the effect of the same amount of unbound isoproterenol injected into the same guinea pig heart. It was noted that the derivatives of the present invention exhibited the effect of the isoproterenol 4 to 5 times longer than when the heart was simply injected with the parent isoproterenol.

A comparison of the specific activity of the derivatives and the parent and related catecholamines is set forth in FIGURE 1 which carries the following legend:

FIGURE 1: Positive chronotropic effects of L-isoproterenol (Δ—Δ); 1500 MW polymeric L-isoproterenol derivative (Δ—Δ) 10,000 MW polymeric L-isoproterenol derivative O—O); L-epinphrine (O—O); 6-amino-L-isoproterenol (□—□); and the 10,000 MW polymeric l-isoproterenol derivative in the presence of D,L-propranolol (5 × 10$^{-7}$ M) (□—□). The doses of the polymeric isoproterenol derivatives are plotted as the total moles of isoproterenol added. The error bars represent the standard error of the mean of each point; the number of experiments for each point is indicated in parentheses. Responses are plotted as the percentage of the maximum change in heart rate of isolated perfused guinea pig hearts which were rapidly dissected from heparinized guinea pigs (300–500 g) and suspended via an aortic cannula in a modified Langendorff apparatus. The FIGURE illustrates that the specific activity of the derivatives is comparable with that of the parent catecholamine. An analysis of the derivative prior to and following the biological testing of the heart established that there was no free catecholamine contained in the derivative solution. Thus, all of the hormone activity can be attributed to the polypeptide derivative of the catecholamine which is effective 4 to 5 times longer.

Similar results were obtained when the derivatives were added to isolated cat papillary muscles.

The invention may be embodied in other specific forms without departing from the spirit or central characteristics thereof. Present embodiments are therefore to be considered as being illustrative and not restrictive, the scope of the invention being indicated by the dependent claims rather than by the foregoing description and all changes which come within the meaning and range of equivalency of the claims are therefore intended to be embraced therein.

We claim:

1. A water-soluble, physiologically active polymer having a high degree of physiological activity over a prolonged period of time, said polymer comprising a water-soluble, linear copolypeptide of an aromatic amine-substituted amino acid and at least one dissimilar amino acid, said copolypeptide having attached to the copolypeptide backbone at least one substituent having the structure:

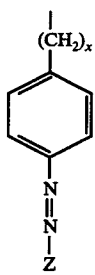

wherein Z is selected from the group consisting of a catecholamine, morphine, an antibiotic, steroid, reserpine, α-methyl dihydroxyphenylalanine, L-dihydroxyphenylalanine, serotinin, carbutamide, tyrosine-containing peptide hormone, gastrin, and substituted phenethylamine group, and $x$ is an integer equal to 0 or 1.

2. The water, physiologically active polymer of claim 1 wherein the copolypeptide comprises an irregular copolymer of a hydroxyalkyl-glutamine and p-aminophenylalanine diazotized to the physiologically active units having the following structure:

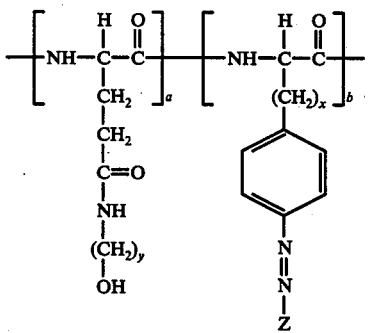

wherein $y$ is an integer of 2 or 3, $x$ is an integer equal to 1, Z is defined as in claim 1, and $a$ and $b$ are integers, the ratio of $a$ to $b$ being in the range 1:1 to 25:1.

3. The water-soluble physiologically active polymer of claim 1 wherein the copolypeptide comprises an irregular copolymer of glutamic acid and p-aminophenylalanine diazotized to the physiologically active units having the following structure:

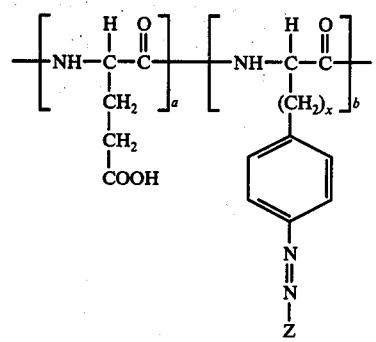

wherein Z is defined as in claim 1, $x$ is an integer equal to 1, and $a$ and $b$ are integers, the ratio of $a$ to $b$ being in the range 1:1 to 25:1.

4. The physiologically active polymer of claim 1 wherein Z is a catecholamine group.

5. The physiologically active polymer of claim 4 wherein the catecholamine group is selected from the group consisting of epinephrine, norepinephrine or isoproterenol.

6. The physiologically active polymer of claim 5 wherein the catecholamine group is epinephrine or isoproterenol.

7. The physiologically active polymer of claim 5 wherein the catecholamine group is norepinephrine.

8. The water-soluble, physiologically active polymer of claim 1 wherein the copolypeptide comprises an irregular copolymer of a hydroxyalkylglutamine and p-aminophenylalanine diazotized to the physiologically active units having the following structure:

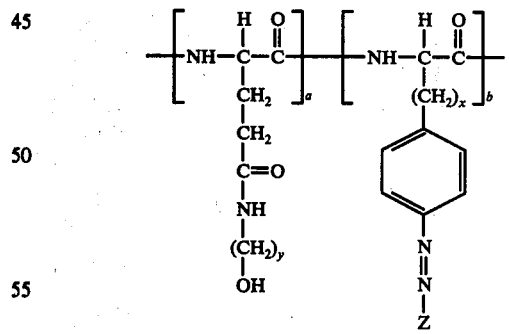

wherein $y$ is an integer of 2 or 3, $x$ is an integer equal to 1, Z is defined as in claim 1, and $a$ and $b$ are integers, the ratio of $a$ to $b$ being in the range 1:1 to 25:1.

9. The water-soluble, physiologically active polymer of claim 1 wherein the copolypeptide comprises an irregular copolymer of glutamic acid and p-aminophenylalanine diazotized to the physiologically active units having the following structure:

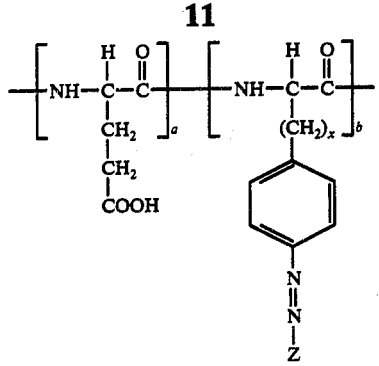

wherein Z is defined as in claim 1, x is an integer equal to 1, and a and b are integers, the ratio of a to b being in the range 1:1 to 25:1.

10. The water-soluble, physiologically active polymer of claim 8, wherein y is 3, x is 1, Z is a catecholamine group and the molecular weight of the copolypeptide is less than 20,000.

11. The water-soluble, physiologically active polymer of claim 10 wherein Z is an epinephrine or norepinephrine group.

12. The water-soluble, physiologically active polymer of claim 10 wherein Z is an isoproterenol group.

* * * * *